United States Patent [19]

Stahly

[11] Patent Number: 4,521,345

[45] Date of Patent: Jun. 4, 1985

[54] AROMATIC COUPLING PROCESS

[75] Inventor: G. Patrick Stahly, Baton Rouge, La.

[73] Assignee: Ethyl Corporation, Richmond, Va.

[21] Appl. No.: 607,272

[22] Filed: May 4, 1984

[51] Int. Cl.$^3$ .......................................... C07C 121/75
[52] U.S. Cl. ................................................. 260/465 F
[58] Field of Search .................................... 260/465 F

[56]     References Cited
       U.S. PATENT DOCUMENTS 4,172,151  10/1979  Moore ................................ 424/330

FOREIGN PATENT DOCUMENTS 2336551  12/1973  Fed. Rep. of Germany .

OTHER PUBLICATIONS

Caronna et al., Tetrahedron Letters, No. 7, pp. 657–660.

Primary Examiner—Dolph H. Torrence
Attorney, Agent, or Firm—Donald L. Johnson; John F. Sieberth; Patricia J. Hogan

[57]     ABSTRACT 4-(2-Cyano-4-nitrophenyl)phenols are prepared by reacting a 3-cyano-1-nitrobenzene having a replaceable hydrogen in the 4-position with a phenol having a replaceable hydrogen in the 4-position in an inert solvent and in the presence of a strong base. The 3-cyano-1-nitrobenzene and phenol may be substituted or unsubstituted, and preferred phenols include phenol and 2,6-dialkylphenols.

11 Claims, No Drawings

AROMATIC COUPLING PROCESS

FIELD OF INVENTION

This invention relates to 4-(2-cyano-4-nitrophenyl)-phenols and more particularly to a process for preparing them.

BACKGROUND

As indicated in Caronna et al., *Tetrahedron Letters*, No. 7, pp. 657-660 (1979), U.S. Pat. No. 4,172,151 (Moore), and German Offenlegungsschrift No. 2,336,551 (Sandoz), unsymmetrically substituted biphenyls are useful as pharmaceuticals, agricultural chemicals, antioxidants, specialty chemicals, and intermediates therefor; and they can be prepared by a variety of techniques. Unsymmetrically substituted biphenyls include 4-(2-cyano-4-nitrophenyl)phenols.

SUMMARY OF INVENTION

An object of this invention is to provide a novel process for preparing 4-(2-cyano-4-nitrophenyl)phenols.

Another object is to provide such a process wherein the 4-(2-cyano-4-nitrophenyl)phenols are prepared from 3-cyano-1-nitrobenzenes and phenols.

These and other objects are attained by reacting a 3-cyano-1-nitrobenzene having a replaceable hydrogen in the 4-position with a phenol having a replaceable hydrogen in the 4-position in an inert solvent and in the presence of a strong base to form a 4-(2-cyano-4-nitrophenyl)phenol.

DETAILED DESCRIPTION

3-Cyano-1-nitrobenzenes utilizable in the practice of the invention are 2-cyano-1-nitrobenzenes having a replaceable hydrogen in the 4-position, any other free position optionally bearing an inert substituent. A preferred 3-cyano-1-nitrobenzene is 3-cyano-1-nitrobenzene itself.

Phenols that can be used in the invention are phenol itself and other phenols having a replaceable hydrogen in the 4-position. Such phenols, when substituted, have inert substituents, such as alkyl, alkoxy, alkenyl, alkynyl, cycloalkyl, aryl, aralkyl, and alkaryl groups, in one or more of the free positions, generally an alkyl group containing about 1-6 carbons, such as methyl, ethyl, propyl, butyl, t-butyl, pentyl, hexyl, etc. Preferred phenols include phenol and 2,6-dialkylphenols, such as 2,6-di-t-butylphenol, 2,6-diisopropylphenol, 2-t-butyl-6-methylphenol, etc. Although the amount of this ingredient employed is not critical, it is generally desirable to use at least a stoichiometric amount of the phenol.

The solvent used in the reaction of the invention may be any solvent that is inert under the conditions of the reaction, i.e., any solvent that will not prevent the reaction from occurring. Exemplary of the solvents that can be used are inert liquid hydrocarbons, such as benzene, toluene, xylene, hexane, heptane, isooctane, etc.; ethers, such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines, such as pyridine, N-ethylpiperidine, triethylamine, tributylamine, N,N-diphenyl-N-methylamine, N,N-dimethylaniline, etc.; alcohols, such as methanol, ethanol, propanol, etc.; nitriles, such as acetonitrile, etc. However, the preferred solvents are dipolar aprotic solvents, such as dimethylsulfoxide, N,N-dimethylformamide, N,N-dimethylacetamide, dimethylsulfone, tetramethylene sulfone, N-methylpyrrolidinone, etc. It is not necessary for the solvent to be anhydrous.

Bases useful in the practice of the invention include all bases strong enough to activate the reactants but are generally alkali metal hydrides, hydroxides, or alkoxides, such as sodium or potassium hydride or hydroxide, sodium methoxide, potassium t-butoxide, etc. If desired, the base can be used in conjunction with a phase transfer catalyst, such as a quaternary ammonium salt, a polyethylene glycol, or a suitable crown ether, as in similar processes known in the art. It is preferable to employ at least one molar proportion of base per molar proportion of the 3-cyano-1-nitrobenzene, although lesser amounts are also satisfactory.

The process of the invention is an oxidation-reduction reaction wherein the phenol is coupled to the 4-position of the 3-cyano-1-nitrobenzene. It may be conducted at any suitable temperature, the most appropriate temperature varying with the strength of the base and reactivities of the reactants employed, to prepare the product in a matter of minutes or a few hours. Ambient temperatures are satisfactory when the strongest bases and/or more reactive reactants are used, but higher temperatures, e.g., temperatures up to about 200° C., are more appropriate when somewhat weaker bases and/or less reactive reactants are utilized. If desired, the reaction mixture may contain optional additives, such as potassium permanganate, which increase the yield of product.

The following example is given to illustrate the invention and is not intended as a limitation thereof.

EXAMPLE

A mixture of 30 mg (0.75 mmol) of powdered sodium hydroxide, 87 mg (0.59 mmol) of 3-cyano-1-nitrobenzene, 155 mg (0.75 mmol) of 2,6-di-t-butylphenol, and 1.0 mL of dimethylsulfoxide was heated at 80° C. for 90 minutes and poured into 10 mL of 1N HCl, and the resulting aqueous mixture was extracted with three 10 mL portions of diethyl ether. The ether layers were combined, dried over magnesium sulfate, and concentrated. Purification of the residue by preparative thin layer chromatography and crystallization afforded 98 mg (47% yield) of 2,6-di-t-butyl-4-(2'-cyano-4'-nitrophenyl)phenol.

It is obvious that many variations can be made in the products and processes set forth above without departing from the spirit and scope of this invention.

I claim:

1. A process which comprises reacting a 3-cyano-1-nitrobenzene having a replaceable hydrogen in the 4-position with a phenol having a replaceable hydrogen in the 4-position in an inert solvent and in the presence of a strong base to form a 4-(2-cyano-4-nitrophenyl)phenol.

2. The process of claim 1 wherein the 3-cyano-1-nitrobenzene is 3-cyano-1-nitrobenzene.

3. The process of claim 1 wherein the phenol is phenol.

4. The process of claim 1 wherein the phenol is a substituted phenol bearing at least one inert substituent on the ring.

5. The process of claim 4 wherein the substituted phenol is a 2,6-dialkylphenol.

6. The process of claim 1 wherein the strong base is an alkali metal hydride, hydroxide, or alkoxide.

7. The process of claim 6 wherein the strong base is an alkali metal hydroxide.

8. The process of claim 7 wherein the alkali metal hydroxide is sodium hydroxide.

9. The process of claim 1 wherein the inert solvent is a dipolar aprotic solvent.

10. The process of claim 9 wherein the dipolar aprotic solvent is dimethylsulfoxide.

11. 2,6-Di-t-butyl-4-(2'-cyano-4'-nitrophenyl)phenol.

* * * * *